United States Patent [19]

Smith, Jr.

[11] 3,965,203

[45] June 22, 1976

[54] PROCESS FOR THE PRODUCTION OF 2-CHLOROBUTADIENE-1,3 FROM 3,4-DICHLOROBUTENE-1

[75] Inventor: Lawrence A. Smith, Jr., Houston, Tex.

[73] Assignee: Petro-Tex Chemical Corporation, Houston, Tex.

[22] Filed: Jan. 31, 1974

[21] Appl. No.: 437,906

[52] U.S. Cl. ............................................. 260/655
[51] Int. Cl.$^2$........................................ C07C 21/20
[58] Field of Search......................... 260/655, 654 D

[56] References Cited
UNITED STATES PATENTS 3,079,446  2/1963  Mac Farlane...................... 260/655

FOREIGN PATENTS OR APPLICATIONS 42-25054  11/1967  Japan................................. 260/655
1,197,539   7/1970  United Kingdom................ 260/655

Primary Examiner—D. Horwitz
Attorney, Agent, or Firm—N. Elton Dry; Kenneth H. Johnson

[57] ABSTRACT

A process is described whereby 2-chlorobutadiene-1,3 is produced from 3,4-dichlorobutene-1 in a two-phase reaction system wherein the reaction predominantly occurs in the organic phase and the production of undesirable by-products, particularly 1-chlorobutadiene-1,3 and acetaldehyde, is suppressed. The practice of the process results in a brine effluent from the reactor containing small amounts of organic materials resulting in a waste product which is less polluting and more easily cleaned.

The organic phase is selected from primary and secondary alcohols, alkoxyethanols and mixtures thereof, preferably alkoxyethanols wherein the alkyl group has two or more carbon atoms. Surprisingly, I have discovered that the selection of the organic phase of the reaction system is made by a screening test wherein a two-phase system of a 20% brine and 3,4-dichlorobutene-1 is prepared and the alcohol or alkoxyethanol being investigated is added to obtain equilibrium in the system. Materials selected as the organic phase material are selected from those where the product of the weight percent water in the organic phase and weight percent alcohol being investigated in the organic phase is greater than 200.

11 Claims, No Drawings

PROCESS FOR THE PRODUCTION OF 2-CHLOROBUTADIENE-1,3 FROM 3,4-DICHLOROBUTENE-1

BACKGROUND OF THE INVENTION

The present invention relates to the production of chloroprene-2 (2-chlorobutadiene-1,3) from 3,4-dichlorobutene-1 by reaction with an alkali metal hydroxide.

A method for producing chloroprene in an aqueous solution of an alkali metal hydroxide is described in U.S. Pat. No. 2,430,016. However, in practicing the aqueous process, the product distribution is not always satisfactory and the reaction time is long. The product distribution, i.e., production of acetaldehyde and 1-chlorobutadiene is excessive, causes, in part, lower yields of desired product. Operation of this process is undesirable because the problem of producing a brine solution free of organic compounds, particularly aldol condensation products and hydrolysis substitution products, is difficult. In order to eliminate these problems, it has been attempted to produce chloroprene in an anhydrous system, particularly alcoholic alkalis, as described in U.S. Pat. No. 2,180,115. While acetaldehyde and 1-chlorobutadiene production is reduced, insoluble solids, particularly sodium chloride, are produced from the reaction, and recovery of the product and solvent is difficult.

Alcohols have also been added to reaction systems in small amounts as catalysts for the reaction with the alkali metal hydroxide (see U.K. Pat. No. 1,218,869). The alcohol was disclosed in the patent as acting as a transfer agent to bring the feed into the aqueous phase to contact the alkali metal hydroxide. While rates and product distribution were improved, however, it was necessary to maintain caustic concentration at above 25%, resulting in disadvantages of the process. The use of a hydrocarbon such as xylene as the reaction medium is disclosed in U.S. Pat. No. 3,026,360, but no improvement in product distribution results and the reaction is retarded.

Homogenous solutions of brine and ether-alcohols are described in U.S. Pat. No. 3,079,446 wherein the reaction takes place in a solution of an ether-alcohol in the brine. The reaction system of said U.S. Pat. No. 3,079,446 is described as having from 10% to 50% by volume ether-alcohol solvent with respect to the volume of water present, resulting in a reaction system having a maximum of 33% an ether alcohol or water soluble cyclic ether. Although some improvement results, as with the other prior methods for producing chloroprene, this method also is fraught with difficulties and undesirable side reactions result. It is particularly true with respect to contamination of the brine to be disposed of.

Previously, experimenters, even those who employed alcohols in the reaction system, turned their attention to the reaction occurring in an aqueous system. Surprisingly, I have discovered that the practice of my invention gives the advantages these experimenters have been searching for. Yet it is my invention to use a two-phase reaction system wherein substantially all of the reaction occurs in the organic phase. Heretofore, this had not been done.

SUMMARY OF THE INVENTION

Surprisingly, I have discovered that, by the use of a two-phase system, with the reaction being conducted in the organic phase, wherein this organic phase is selected from a primary or secondary alcohol, an alkoxyethanol or mixtures thereof, meeting a certain test discovered by me hereinafter described, produces surprisingly advantageous yields of chloroprene from 3,4-chlorobutene-1 and, further, wherein the reaction system has an organic phase of from about 40% to about 90% by volume. The process is equally adapted for batch or continuous processes.

I have surprisingly found that when the product of the percent water and percent alcohol in the 3,4-dichlorobutene-1 phase of a two-phase mixture of 3,4-dichlorobutene-1 and water, at equilibrium, is greater than 200, the alcohol or alkoxyethanol is satisfactory for use as the organic phase material. When the material meets the test, high yields and high selectivity of 2-chlorobutadiene-1,3 results without consequent production of undesirable 1-chlorobutadiene-1,3, acetaldehyde and other unwanted by-products, particularly aldol condensation products and hydrolysis substitution contaminants. This allows the easy removal of organics from the aqueous phase brine and easy recovery of the 2-chlorobutadiene-1,3 product from the reaction vessel, resulting in greater process efficiency and less pollution from disposal of waste brine.

DESCRIPTION OF THE PREFERRED EMBODIMENTS

In the dehydrohalogenation of 3,4-dichlorobutene-1 to produce 2-chlorobutadiene-1,3, the reaction is carried out by reacting alkali metal hydroxides such as sodium hydroxide, potassium hydroxide, or calcium hydroxide and the like with the feed compound, forming water and the alkali metal chloride. In the reaction, the hydroxide is present in a slight excess such as from 1 to 2 moles hydroxide per mole of 3,4-dichlorobutane-1, and preferably from 1.02 to about 1.4 moles since larger excess is not necessary but may be present. Since the process of my invention results in the utilization of substantially all the hydroxide present, very low ratios may be used. This results in greater efficiency in the process.

The reaction occurs, with stirring, at a temperature of from about 75°C. to about 125°C. and preferably from about 85°C. to about 110°C. The pressure at which the reaction is carried out is generally atmospheric pressure or a pressure slightly above atmospheric pressure, such as from about 5 to 10 psig. While higher pressures may be used, no advantage is seen to result therefrom. These parameters of the operation of the method are well-known to those skilled in the art as described in many of the above-mentioned patents are equally applicable to the practice of my invention.

While applicable to batch operation, the practice of my invention is particularly applicable to a continuous process whereby the reactor is charged with the desired amounts of water to form the liquid phase and an initial charge of the primary or secondary alcohol, alkoxyethanol or mixtures thereof to be used as the organic phase. The alkyl group of the alkoxyethanol will generally be an alkyl group having at least 2 carbon atoms. The water and the organic material form a two-phase reaction system wherein from about 40% to about 90% by volume of the system is organic phase, and preferably from about 60% to about 80% by volume.

Alkali metal hydroxide is charged to the system such that the aqueous layer is approximately 20% by weight of the solids, i.e., the hydroxide and the salt. The alkali metal hydroxide may vary in initial strength from about 2 wt.% to about 25 wt.% of the water or even to the saturation point of the brine. However, at low concentrations, the aqueous phase becomes large and cumbersome and there is a tendency toward precipitation of the salt formed at higher concentrations.

After the reactor is heated to the reaction temperature selected within the range as hereinbefore set forth, feed is begun whereby the 3,4-dichlorobutane-1, organic phase material, and a solution of the alkali metal hydroxide, usually at a 20 wt.% concentration, though the concentration may be varied as set forth above, is continuously fed to the reactor which is stirred during reaction. During the reaction, the chloroprene product is removed overhead through a column where it is separated from any intermediate boiling impurities, such as the dichlorobutanes and vinylcyclohexenes, with the final product being sent to storage. The impurities and recovery of unreacted 3,4-dichlorobutene-1 are carried out by separation methods, such as fractional distillation, well-known to those skilled in the art. These separation methods will vary according to physical characteristics, such as boiling point and the organic phase material chosen. It is preferred to use 2-butoxyethanol since its boiling point is sufficiently high to facilitate separation and recovery.

During the reaction, portions of the aqueous phase in the reactor are removed in order to remove the accumulation of brine formed during the reaction. In the practice of my invention utilizing the two-phase solvent system, since there is a very low production of hydrolysis substitution contaminants as opposed to the aqueous phase systems, the brine contains less organic material and is easily cleaned, by steam stripping, for example, for disposal. The method of removing organics from the brine is well-known to the skilled engineer. Again, 2-butoxyethanol shows particular advantages as the material selected for the organic phase of the two-phase reaction system. The brine produced using 2-butoxyethanol as the organic phase is clean, affording easy processing for disposal. In carrying out the reaction in a continuous manner, the reactants and components of the two-phase reaction system are fed at such a rate to maintain a substantially constant reaction volume in the proportions hereinbefore set forth, with the volume also maintained by the removal of chloroprene overhead and withdrawal of portions of the organic and aqueous phase from the reactor, preferably through a phase separation vessel.

Since the reaction occurs in the organic phase where it is fast and the residence time of the chloroprene product is low, there is little time for heat degradation of the desired product before it is distilled from the reaction medium into the product recovery section of the unit. This, too, is a surprising advantage of my invention.

As criteria. While the criteria hereinbefore, the essence of my invention resides in the use of a two-phase reactor system with the organic phase being selected to meet certain physical and reaction criteria may appear unrelated to the reaction being conducted, I have surprisingly discovered that the success of the two-phase reaction is attributable to the composition of the organic phase with respect to the 3,4-dichlorobutene-1 feed, the organic phase material, i.e., the alcohol or the alkoxyethanol, and water concentration. Since it is necessary to bring caustic into contact with the 3,4-dichlorobutene-1 in order to achieve reaction, both must be present in quantities sufficient for the reaction to proceed at a satisfactory rate. Once reacted, the salt formed would retreat to the aqueous layer with the chloroprene product, and possibly some of the organic phase material, removed overhead. This criteria is more specifically described below and applied to several candidates for use as the organic phase of the reaction system.

In order to verify the selection in accordance with the solubility tests, reactions have been run using 1,4-dichlorobutene-2 to produce 1-chlorobutadiene-1,3 in order to determine the selectivity of this product in the system. The differences between selectivity in the organic phase and the aqueous phase are so gross as to be significant in verifying selection when this feed is used, whereas the difference between selectivities where 3,4-dichlorobutene-1 is used is too small to be significant in verifying the selection. However, the difference in selectivity between aqueous and organic phases, usually about 3%, is of great commercial significance since it is usually the difference between 95% and 98% yield of chloroprene-2.

A good correlation has been found between the product of the percent water and percent alcohol in the organic material phase, selectivity of the reaction product using the 1,4-dichlorobutene-2 and practice of the process of my invention using the 3,4-dichlorobutene-1. Using the above-mentioned criteria, I have found that propanol-1, propanol-2, butanol-1, ethoxyethanol and butoxyethanol are good materials to select to make up the organic phase. In that regard, other materials meeting the criteria will be good organic phase materials. The following discussion relates to the selection procedures for the organic liquid phase material.

SCREENING TEST

Into a separatory funnel, pour 10 ml. 3,4-dichlorobutene, 20 ml. of the alcohol to be tested, and 20 ml. of brine (20 weight percent sodium chloride in water); because of the reactivity of the 3,4-dichlorobutene-1 at room temperature, a brine-sodium hydroxide mixture cannot be used. Shake, let stand until the two phases can be separated, and then centrifuge each of the separated phases if it shows any turbidity. Analyze each phase for water and 3,4-dichlorobutene-1 and calculate the alcohol concentration by difference. The results of various tests are shown in Table I.

TABLE I

| | THE SYSTEM: 3,4-DICHLOROBUTENE-1, ALCOHOL, AND 20 WT. % BRINE | | | | | | |
|---|---|---|---|---|---|---|---|
| | Composition of the Dichlorobutene Phase, Wt.% | | | | Composition of the Aqueous Phase, Wt.% | | |
| Alcohol | Water | 3,4-DCB-1* | Alcohol (by diff.) | (%H$_2$O)× (% Alcohol) | Water | Alcohol (by diff.) | 3,4-DCB-1* |
| Methanol | 0.7 | 96.2 | 3.1 | 2.2 | 55 | 44 | 1 |

TABLE I-continued

THE SYSTEM: 3,4-DICHLOROBUTENE-1, ALCOHOL, AND 20 WT. % BRINE

| Alcohol | Composition of the Dichlorobutene Phase, Wt.% | | | | Composition of the Aqueous Phase, Wt.% | | |
|---|---|---|---|---|---|---|---|
| | Water | 3,4-DCB-1* | Alcohol (by diff.) | (%H$_2$O)× (% Alcohol) | Water | Alcohol (by diff.) | 3,4-DCB-1* |
| Ethanol | 3.1 | 72.5 | 24.4 | 76 | 60 | 38 | 2 |
| Propanol-1 | 6.0 | 40.4 | 53.6 | 322 | 86 | 14 | <1 |
| Propanol-2 | 8.2 | 45.3 | 46.5 | 381 | 88 | 12 | <1 |
| 2-Methyl-Propanol-2 | 3.7 | 62.5 | 33.8 | 125 | 88 | 12 | <1 |
| Butanol-1 | 3.8 | 37.8 | 58.4 | 222 | 92 | 8 | <1 |
| Pentanol-1 | 3.1 | —** | — | — | — | — | — |
| Hexanol-1 | 2.1 | 34.5 | 63.4 | 133 | 93 | 7 | <1 |
| 2-Methoxy-ethanol | 0.9 | 89.3 | 9.8 | 8.8 | 53 | 44 | 1 |
| 2-Ethoxy-ethanol | 6.5 | 51.2 | 42.3 | 275 | 67 | 33 | <1 |
| 2-Butoxy-ethanol | 4.8 | 36.4 | 58.8 | 282 | 85 | 15 | <1 |

*3,4-dichlorobutene-1
**Interference between pentanol and dichlorobutene on GC.

From these data, certain predictions can be made: in systems where the dichlorobutene phase is low in alcohol and/or the aqueous phase is high in alcohol and dichlorobutene, a large portion of the reaction will take place in the aqueous phase. Thus, methanol, ethanol, and 2-methoxyethanol are bad solvents for both of these reasons since it is desirable that substantially all of the reaction takes place in the organic phase.

Therefore, the correlation of the data resulting from the screening test involves the interrelation of the amount of water and alcohol in the organic phase. Thus, the product of these two concentrations has been surprisingly found to be accurate for selection of the organic phase and I have found that those candidates wherein this product is greater than about 200 are satisfactory for use in the practice of my invention. Thus, it is seen from Table I that propanol-1, propanol-2, ethoxyethanol and butoxyethanol are good organic phase materials.

VERIFICATION TEST

The results of the screening test are verified by running semi-micro dehydrochlorinations of 1,4-dichlorobutene-2 since this reaction shows marked differences of reaction products between the reaction taking place in the aqueous phase and the organic phase. If it is reacted with base in essentially anhydrous conditions (so that the substitution reaction is small compared to elimination), 1-chlorobutadiene is the product. Reaction with alkali hydroxide (in an aqueous system) makes acetaldehyde and aldol products. The reasoning behind the use of this feed for the verification test has been previously described.

Into the 100 ml. flask equipped with an electric heating mantle, a magnetic stirrer, packed column with a condenser and an ice-cooled receiver, pour 20 to 22 ml. of 20 wt.% sodium hydroxide solution (24–27 grams) and 30 ml. of the alcohol to be tested. Weigh about 10 ml. of 1,4-dichlorobutene-2 in a syringe, add the contents to the flask, and determine the empty weight of the syringe. Stopper the flask; turn on the magnetic stirrer, the variable transformer to the heating mantle, and the cooling water to the condenser. Note the time and insulate the top of the flask and the distillation column with asbestos tape. Remove the water/alcohol/1-chlorobutadiene azeotrope as it distills out of the flask (complete removal is not necessary since products and flask residue will be recombined later). After two hours, turn off the heat, remove the insulation and the mantle, and carefully cool the flask. Pour all overhead product and flask contents into a separatory funnel. Wash the column, reflux head, condenser, flask and receiver with alternate portions of water and alcohol under study and then with toluene; add the washings to the separatory funnel. (In the butanol case, or when butanol is used as an internal standard, use m-xylene instead of toluene because toluene and butanol elute together on the chromatographic column used.)

Shake the mixture in the funnel and carefully separate the toluene (or xylene) layer from the aqueous layer and add the toluene layer to a tared bottle. Repeat the extraction twice, each time adding the aromatic layer to the tared bottle. Determine the total weight of the extract and analyze by using well-known gas chromatographic methods. In performing this test, a Varian Model 1800 instrument was used. Calculate the selectivity of the reaction to 1-chlorobutadiene as follows:

$$\text{Selectivity (G/100 G 1,4-DCB-2 Reacted)} = \frac{(\text{G 1-chlorobutadiene produced}) \times 100}{(\text{G Impure 1,4-DCB-2 Added})-(\text{G 3,4-DCB-1 in 1,4-DCB-2})-\text{G 1,4-DCB-2 (Unreacted)}}$$

The results of verification of screeing tests are shown in Table II.

TABLE II

THE EFFECT OF SOLVENT IN ORGANIC PHASE ON THE DEHYDROCHLORINATION OF 1,4-DICHLOROBUTENE-2

| Solvent System | Selectivity 1-Chlorobutadiene, G/100G 1,4-DCB-2 Reacted |
|---|---|
| Water | 3.5 |
| Methanol + Water | 2.4 |
| Ethanol + Water | 8.8 |
| Propanol-1 + Water | 16.8 |
| Propanol-2 + Water | 16.9 |
| 2-Methylpropanol-2 + Water | 8.6 |
| Butanol-1 + Water | 13.4 |
| Pentanol-1 + Water | 12.8 |
| Hexanol-1 + Water | 9.8 |
| 2-Methoxyethanol + Water | 12.9 |
| 2-Ethoxyethanol + Water | 18.1 |
| 2-Butoxyethanol + Water | 19.7 |
| Anhydrous (Butanol + Solid NaOH) | 26.3 |

TABLE II-continued

THE EFFECT OF SOLVENT IN ORGANIC PHASE ON THE
DEHYDROCHLORINATION OF 1,4-DICHLOROBUTENE-2

| Solvent System | Selectivity 1-Chlorobutadiene, G/100G 1,4-DCB-2 Reacted |
|---|---|
| Anhydrous (2-Butoxyethanol + Solid NaOH) | 39.0 |

Hexanol, ethanol, and methanol are also shown to be very poor reaction media. Some interesting relationships exist between these selectivities and the compositions of the 3,4-DCB-1 phases in Table I. If selectivity to 1-chlorobutadiene from Table II in simple alcohol systems is plotted versus either alcohol concentration or 3,4-DCB-1 concentration in the 3,4-DCB-1 phase of the screening test (Table I), the selectivity goes through a maximum at about fifty percent alcohol and 40–45% 3,4-DCB-1. Of the lower alcohols tested, tertiary butyl alcohol (2-methyl-propanol-2) failed the screening test, thus the exclusion of tertiary alcohols from the practice of my invention. In the alkoxyethanol systems tested, the selectivity curve is generally higher indicating that, as a class, they are expected to be better candidates than a simple alcohol. Water concentration in the 3,4-DCB-1 phase shows a rough correlation with selectivity: the higher the water concentration, the higher the selectivity to 1-chlorobutadiene.

The center column of Table I tells the product of percent water and percent alcohol in the 3,4-DCB-1 phase and it is this FIGURE upon which selection is made. This product is proportional to the selectivity to 1-chlorobutadiene in the verification test and thus is used as the guideline to select the material to make up the organic phase of the two-phase reaction system of my invention. Those materials having a product greater than 200 are acceptable and those having a product greater than 250 are preferred.

The following examples are offered to be illustrative of the practice of my invention and of the validity of the surprising discovery related thereto and should not be considered to be limiting of the described invention.

EXAMPLE I

While my process is applicable to batch operation, this example describes the method of my invention using continuous operation and demonstrates many of the advantages achieved thereby.

A stirred laboratory dehydrochlorinator made from a 3-neck resin kettle flask with baffles and a bottom tap was fitted with a 25 tray 1 inch Oldershaw column which has a vapor side draw at tray 10 (counting from the bottom). The reflux head of the column is liquid dividing and magnetically controlled by an electric reflux timer in conjunction with a temperature controller. The condensers and receivers are kept at 0°–5°C. by circulating a refrigerated water-ethylene glycol solution through their jackets. The reactor vessel is mechanically agitated with a paddle-type stirrer and the glass stirrer bearing is liquid sealed and lubricated using reactor brine effluent. Inlets are available for pumping reactants or taking samples and a bottom opening connects directly to a 500 ml. decanter. Heat is provided by an electric mantle.

Initially, a decanter attached to the bottom tap of the flask was filled with 300–350 ml. of brine and 150–200 ml. of 99.5% 2-butyoxyethanol. The reactor was charged with 700–750 ml. of 99.6% 2-butoxyethanol and 100 ml. of water. The system was nitrogen purged and heated to 95°–100°C. before 3,4-dichlorobutene-1 and caustic were introduced through one the necks of the flask. Operation was manual until the desired inventories and temperatures were established.

At equilibrium, the total reactor liquid level was about one liter including reactants and suspended brine solution. Constant heat was applied and the system was controlled automatically by using the temperature at tray 10 to control the overhead take-off and the reaction liquid temperature to direct the 3,4-dichlorobutene-1 feed. Specifically, a setting of 140°F. at tray 10 alternately decreased or increased the reflux rate for fluctuations above or below that temperature. Similarly, a reaction liquid temperature of 202°F. was set to control the 3,4-dichlorobutene feed. The system is operated at substantially atmospheric pressure.

The rate of chloroprene production was determined by setting a fixed NaOH addition and brine was pumped out at a rate which maintained a constant level in the decanter where phase separation occurred. The side stream draw on the column at tray 10 was set to remove about 10% of the amount being taken off overhead.

Periodic reaction liquid samples were removed and fresh 99.6% 2-butoxyethanol was added to replace sampling loss plus that lost in the brine.

Using the described system, a 12-hour continuous run was performed under the following conditions:

Rates:

| | |
|---|---|
| NaOH (18 wt.%) | 3.60 moles/hr. |
| 3,4-DCB-1 (99 wt.%) | 3.23 moles/hr. |
| Chloroprene: | |
| Overhead | 2.84 moles/hr. |
| Side Draw (Tray 10) | .34 moles/hr. |
| Reflux Ratio | 1.9:1 |

Profile:

| Tray | Temp. | Chloroprene,% | 1-Cl-Bd, % | %VCH[2] & DC Banes | % 3,4-DCB-1 | % 2-Butoxy Ethanol |
|---|---|---|---|---|---|---|
| 25 | 131°F. | 99.2 | .8 | — | — | — |
| 10 | 140°F. | 95.8 | 2.0 | 1.2 | 1.0 | — |
| Reactor | 202°F. | 4.4 | — | 1.3 | 6.6 | 85.5[1] |

[1]This is a GC Flame Detector valve which excludes water.
[2]VCH — vinylcyclohexene; DC Banes — dichlorobutanes.

Brine Analysis:

23.0 % NaCl
2.0 % NaOH
.7 % 2-butoxyethanol (G.C.)
.46% Total Carbon

The foregoing brine analysis illustrates the low carbon content of the brine phase resulting predominantly from the 2-butoxyethanol which is easily removed and the good utilization of the caustic charged. Even better utilization has been achieved with improved agitation. No inhibitors were added to the dehydrochlorinator and the system was kept in equilibrium with a reservoir of nitrogen at atmospheric pressure during the run.

The product chloroprene was not further treated except for addition of 500–600 ppm butylated hydroxytoluene and nitrogen blanketed before freezer storage.

Three quarts of material were collected from this run and the most impure sample was analyzed as follows:

| Component | |
|---|---|
| $C_4$'s | 15 ppm |
| Acetaldehyde | 2 ppm |
| Monochlorobutanes | 339 ppm |
| 1-Chlorobutadiene-1,3 | .74 % |
| Chloroprene | 99.0 % |

EXAMPLES II–IV

In the same manner as described in Example I above, other continuous runs have been made, except that a two-section column is used with an upper section having 10 trays and a lower section with three trays. The temperature control is set at tray three of the lower section. The results are set forth on Table III below. Also included is a comparative run using water alone. No chloroprene was produced when 2-methylpropanol-2 (tert-butyl alcohol) having a product of 125 from Table I and n-hexanol, product of 133, were used as the organic phase, further demonstrating the validity of my criteria.

TABLE III

| Example | II | III | IV |
|---|---|---|---|
| Organic Phase Material | None | Propanol-1 | Butanol-1 |
| Reaction Temperatures | | | |
| Pot (Vapor) | 86°C | 81°C | 87°C |
| Tray 3 | 135°F | 133°F | 134°F |
| Overhead | 54°C | 54°C | 54°C |
| Feed Rates (mole/hr.) | | | |
| 20% NaOH | .96 | 1.75 | 3.46 |
| 3,4-DCB-1 | .81 | 1.47 | 2.24 |
| Length of Run, hrs. | 4 | 5 | 4 |
| Overhead Product Distribution | | | |
| Chloroprene, wt.% | 97.3 | 97.3 | 98.6 |
| 1 Cl-butadiene, wt.% | 2.5 | 1.3 | 1.3 |
| Acetaldehyde, ppm | 696 | <100 | <100 |
| Organic Phase, % | — | 1.4 | 0 |
| Chloroprene Production Rate (moles/hr.) | 0.71 | 1.40 | 2.10 |

EXAMPLE V

This example illustrates a batch dehydrochlorination of 3,4-dichlorobutene-1 using propanol-2 as the organic phase material.

The reactor was a 2-liter, three-neck indented round-bottom flask employing a magnetic stirring bar for agitation. It was fitted with an addition funnel, nitrogen bleed, Friedrichs condenser, and a dry ice trap. Ice water was circulated through the Friedrichs condenser and provision was made to permit the reflux to be drawn off if desired. A slow nitrogen bleed was permitted to pass through the reactor and condenser to the dry ice trap. This stream carried with it product chloroprene which was condensed in the trap.

The reactor was charged with 300 gm. of 5 wt.% aqueous NaOH and 200 gm. of propanol-2 at about 160°F. To this was added 27 ml. 3,4-DCB-1 (0.1 wt.% 1,4-DCB-2) and the reaction was run, with mixing for 54 minutes. The conversion was 100%, the ice trap contained 21.5 gm. material and the product analysis is shown as follows:

| | |
|---|---|
| Chloroprene, % | 98.8 |
| 1-Chlorobutadiene, % | 1.2 |
| Acetaldehyde, ppm | Nil |
| Polymer, gm. | 0.02–0.05 |

Having thus described my invention, those skilled in the art will be able to make many modifications and variations thereof without departing from the scope and spirit of the appended claims.

I claim:

1. In the process for the preparation of 2-chlorobutadiene-1,3 by the dehydrohalogenation of 3,4-dichlorobutene-1 by reaction with a stoichiometric excess of an alkali metal hydroxide and recovery of the 2-chlorobutadiene-1,3, the improvement which comprises:

contacting, at a temperature of from about 75°C. to about 125°C., the 3,4-dichlorobutene-1 with the alkali metal hydroxide in a two-phase reaction system having an organic phase and an aqueous phase wherein substantially all the reaction occurs in the organic phase of said system;

further, wherein the organic phase is from about 40% to about 90% by volume of the entire system, the organic phase being a material selected from primary or secondary alcohols, alkoxyethanols or mixtures thereof which, when added to a two-phase system of 3,4-dichlorobutene-1 and a 20 wt.% brine solution, at equilibrium, has a solubility in the dichlorobutene phase such that the product of the weight percent water and the weight percent organic phase material present in the dichlorobutene phase is greater than 200.

2. The process of claim 1 wherein the organic phase of the reaction system is propanol-1.

3. The process of claim 1 wherein the organic phase of the reaction system is propanol-2.

4. The process of claim 1 wherein the organic phase of the reaction system is butanol-1.

5. The process of claim 1 wherein the organic phase of the reaction system is 2-butoxyethanol.

6. The process of claim 1 wherein the organic phase of the reaction system is from about 60 to about 80 volume percent of the reaction system.

7. The process of claim 1 wherein the ratio of alkali metal hydroxide to the 3,4-dichlorobutene-1 is from about 1.02:1 to about 1.4:1.

8. A continuous process for the preparation of 2-chlorobutadiene-1,3 from 3,4-dichlorobutene-1 which comprises:

(a) feeding an aqueous alkali metal hydroxide solution at a concentration of from about 2% to about 25% by weight of the alkali metal hydroxide and 3,4-dichlorobutene-1 to a two-phase reaction system in a mole ratio of 1.02 to about 1.4 moles of the hydroxide per mol of the 3,4-dichlorobutene-1;

(b) contacting the 3,4-dichlorobutene-1 at a temperature of from about 75°C. to about 125°C. with the alkali metal hydroxide in the two-phase reaction system having an organic phase and an aqueous phase wherein substantially all the reaction occurs in the organic phase of said system; further wherein the organic phase is from about 40% to about 90% by volume of the entire system, the organic phase being a material selected from primary or secondary alcohols, alkoxyethanols or mixtures thereof which, when added to a two-phase system of 3,4-dichlorobutene-1 and a 20 wt.% brine solution, at equilibrium, has a solubility in the dichlorobutene phase such that the product of the weight percent water and the weight percent organic phase material present in the dichlorobutene phase is greater than 200;

(c) continuously recovering product chloroprene in an overhead stream; and (d) removing a portion of the reaction system at substantially the same rate as the feed (a) is entering, to remove brine being formed in the aqueous phase.

9. The continuous process of claim 8, wherein the organic phase of the reaction system is 2-butoxyethanol.

10. The continuous process of claim 9, wherein the organic phase is from 60 to about 80 volume percent of the reaction system.

11. The continuous process of claim 10, wherein the ratio of alkali metal hydroxide to the 3,4-dichlorobutene-1 is from about 1.02:1 to about 1.4:1.

* * * * *

UNITED STATES PATENT OFFICE
CERTIFICATE OF CORRECTION

PATENT NO. : 3,965,203
DATED : June 22, 1976
INVENTOR(S) : Lawrence A. Smith, Jr.

It is certified that error appears in the above-identified patent and that said Letters Patent are hereby corrected as shown below:

Column 4, Line 3 reads "As criteria. While the criteria" but should read -- As stated hereinbefore --.

Signed and Sealed this

Fifth Day of June 1979

[SEAL]

Attest:

RUTH C. MASON
Attesting Officer

DONALD W. BANNER
Commissioner of Patents and Trademarks